United States Patent [19]

Khan et al.

[11] Patent Number: 5,609,866
[45] Date of Patent: Mar. 11, 1997

[54] RADIATION STERILIZABLE ANTIMICROBIAL OINTMENT AND PROCESS TO MANUFACTURE

[75] Inventors: Mohammed A. Khan, Sandy; John F. Moellmer, Salt Lake City, both of Utah

[73] Assignee: Becton Dickinson and Company, Franklin Lakes, N.J.

[21] Appl. No.: 163,609

[22] Filed: Dec. 6, 1993

Related U.S. Application Data

[63] Continuation of Ser. No. 884,245, May 11, 1992, abandoned, which is a continuation of Ser. No. 595,719, Oct. 9, 1990, abandoned, which is a continuation of Ser. No. 348,758, Apr. 24, 1989, abandoned.

[51] Int. Cl.$^6$ .............................. A61K 31/79; A61K 2/00
[52] U.S. Cl. ........................... 424/78.25; 422/22; 422/37; 424/667; 424/668
[58] Field of Search ................................ 424/78.32, 667, 424/668

[56] References Cited

U.S. PATENT DOCUMENTS

| Re. 29,909 | 2/1979 | Kurtz | 252/89 R |
|---|---|---|---|
| 4,113,857 | 9/1978 | Shetty | 424/150 |
| 4,364,929 | 12/1982 | Sasmor et al. | 252/518 |
| 4,427,631 | 1/1984 | Bunting et al. | 422/22 |
| 4,569,736 | 2/1986 | Kosegaki et al. | 422/22 |
| 4,671,957 | 6/1987 | Holthousen | 424/80 |

FOREIGN PATENT DOCUMENTS

| 1434550 | 5/1976 | United Kingdom | 424/672 |
|---|---|---|---|
| 1441364 | 6/1976 | United Kingdom | 424/672 |

OTHER PUBLICATIONS

R. E. Glegg, Z. I. Kertesz, Aftereffect in the Degradation of Cellulose and Pectin by Gamma Rays, Nov. 2, 1956, p. 893, New York State Agricultural Experiment Station, Cornell University, Geneva, New York.

R. E. Glegg, The Influence of Oxygen and Water on the After–Effect in Cellulose Degradation by Gamma–Rays, 1957, pp. 469 to 473, Radiation Research.

R. E. Glegg, Z. I. Kertesz, Effect of Gamma–Radiation on Cellulose, 1957, pp. 289 to 297, Journal of Polymer Science.

Technical Data on Pluronic Polyols, BASF Wyandotte Corporation, pp. 1–11.

*Primary Examiner*—Peter F. Kulkosky
*Attorney, Agent, or Firm*—Nanette S. Thomas; Bruce S. Weintraub

[57] ABSTRACT

Sterilized povidone-iodine (polyvinylpyrrolidone-iodine) in an ointment form is obtained by preparation of a mixture of purified water, povidone-iodine, a non-ionic gelling agent, and a non-ionic low suds surfactant. The ointment is a liquid in the temperature range of about 2° C. to 9° C. because of the influence of the non-ionic gelling agent. At room temperature, the mixture forms a free standing ointment which can be sterilized by gamma radiation without degradation of its antimicrobial efficacy, viscosity or shelf life. The ointment is easily prepared by using chilled purified water which maintains the mixture as a liquid while all of the ingredients are mixed together. At room temperature the mixture becomes a free standing ointment.

1 Claim, No Drawings

RADIATION STERILIZABLE ANTIMICROBIAL OINTMENT AND PROCESS TO MANUFACTURE

This is a continuation of application Ser. No. 07/884,245, filed on May 11, 1992, now abandoned which is a continuation of U.S. Ser. No. 07/595,719, filed on Oct. 9, 1990 (now abandoned), which is a continuation of U.S. Ser. No. 07/348,758, filed on Apr. 24, 1989 (now abandoned).

BACKGROUND OF THE INVENTION

1. Field of Invention

This invention relates to the preparation and sterilization of povidone-iodine ointment used for topical disinfection, and more specifically, to the ingredients in the ointment mixture, their relative weight percentages with respect to one another, and how the ingredients are combined into a mixture are also a part of this invention.

2. Background Description

Ointments are recognized as salves or unguents for application to the skin as a semi-solid medicinal preparation. The idea of an ointment is to have a soft unctuous preparation which at room temperature exists as primarily a separate soft free standing solid that does not flow. The ointment should have a wet or moist looking surface appearance with no visible separation of the solid and wet portions.

Povidone-iodine ointments used in the topical antimicrobial treatment of human and animal skin are formulated with povidone-iodine (a complex of povidone and iodine) and contain sufficient iodine in active form to kill microbes. Consequently, povidone-iodine treats wounds and skin abrasions. Topical disinfection solutions containing povidone-iodine are used as cleansing and patient pre-operative preparing agents and are well recognized as a germicidal agent which is safe, non-irritating to the skin and shelf stable for a commercially acceptable period of time. Povidone-iodine powder has been used in making iodophor ointments for topical disinfection.

Polyvinylpyrrolidone is a homo-polymer of 1-ethenyl-2-pyrrolidinone also known as 1 vinyl-2-pyrrolidinone polymer. A common name for this chemical substance is povidone and the compound is sometimes designated as PVP. Povidone is a synthetic polymer having linear 1-vinyl-2-pyrrolidinone groups polymerized into polymer chains of various molecular weights, generally having mean molecular weights ranging from about 10,000 to 700,000. Polymers of both lesser and higher molecular weights are known.

Povidone is available as, either as a dry powder or in aqueous solution for use in a wide variety of chemical, pharmaceutical and food manufacturing processes as well as special industrial compositions such as inks, paints and emulsions, cosmetics and germicidal products. Povidone, in manufacture and formulation of different compositions, contributes to the viscosity of the fluid medium being used. The viscosity contribution of povidone ranges from higher to low viscosity as a function of the average molecular weight of the polymer. Povidone is classified by K-values which are assigned to the various povidone polymers, the smaller the K-value, the lower the intrinsic viscosity of the polymer solution.

The more common commercially available povidone polymers have K-values of K-17, K-30, K-60 and K-90. In aqueous solutions, povidone K-17 and povidone K-30 have little effect on viscosity in concentrations below 10%, whereas povidone K-60 and povidone K-90 have considerable influence on the flow properties of a solution at such concentrations. Moreover, certain organic solvents have a particular effect on the viscosity contribution of povidone, the intensity of which is related to the polarity of the particular organic solvent.

Cross-linkage of the povidone polymer is influenced by diverse factors as for example, actinic light, diazo compounds, oxidizing agents and heat. Cross-linking of the povidone polymer is a serious limitation to its use since the povidone polymer is altered into an aqueous insoluble form. The presence of certain substances in the povidone solution will accelerate cross-linking at even lower temperatures. When a povidone solution is heated to 100° C., in the alkaline pH range, the polymer becomes permanently altered to be irreversibly insoluble. Similar cross-linked changes occur when alkaline sodium phosphate buffers are used and when an oxidizing agent such as ammonium persulfate is added to a povidone solution, cross-linking gel formation occurs in about 30 minutes when the combination is heated at moderate temperatures of about 90° C.

Therefore, aqueous solutions of povidone subjected to autoclaving to sterilize povidone preparations, may cause degradation of the polymer. Thus for example, povidone which is stable to moderate heat will darken in color and decrease in water solubility when heated to about 150° C. The cross-linking of the polymer caused by heat, oxidizing agents, salts and other substances presents special problems in the manufacture and processing of certain compositions containing povidone, when these povidone solutions are intended for parenteral use, since the formed insoluble cross-linked povidone may initiate thrombotic episodes and other noxious events. When povidone is used in the manufacture of those preparations requiring sterilization but containing oxidizing agents or other oxygen sources, then similar incompatibility occurs to limit the use of povidone in the preparations.

For medical products gamma radiation, an effective sterilizing process, is notoriously unsuited for use with povidone polymers. The particular degradative effects followed by cross-linkage and gelation occurring when povidone is exposed to even minimal gamma radiation dosage is well known. The formation of a stable ointment to be subject to gamma radiation is of concern. The actions of radiation on povidone, together with radiolysis products formed in the composition, results in macroradical polymer chain formation and these macroradicals further inter-react so that the ultimate effect of radiation is either cross-linkage gelation or chain scission.

When povidone solutions are irradiated with gamma radiation, gelation occurs when the concentration of povidone in solution is above 0.3% to 1% by weight of povidone. For the lower molecular weight of K-30 and below concentrations between 0.3% and 0.5% are acceptable. Below this critical concentration limit, macrogelation to form a wall-to-wall gel, is not readily observed.

The sensitivity of povidone to low dosages of gamma radiation is so pronounced that adverse gelation crosslinkage effects are observed after irradiation with doses as low as 0.1 kilorad, when the noted concentration of povidone in solution is exceeded. The use of povidone in most industrial, agricultural and pharmaceutical manufacturing procedures exceeds the concentration limits established for the gamma radiation of povidone. The concentration level for povidone is further adversely modified by ionizing solutions, and pH. This destructive, degradative response of povidone to gamma radiation which destroys its desirable properties in the formulation precludes the use of gamma radiation as a means to render povidone and povidone-containing compositions free of microbial contamination.

Thus, attempts to produce sterilized povidone-iodine by irradiation of the povidone prior to formulation of the povidone-iodine are complicated by the described problems of gamma radiation of the povidone. The sterilization of povidone-iodine after formation is found to be unsatisfactory because the irradiation has the effect of decreasing the amount of available iodine with consequent reduction in antibacterial activity. Commercially available povidone-iodine ointments typically thickened by using cellulosic fillers which upon irradiation undergo severe degradation turning into liquids with a water like consistency.

A povidone-iodine ointment which is easy to mix and sterilize without loss of viscosity or antimicrobial activity has not been available. The ability to gamma radiate to sterilize the mixture without viscosity changes to the desired free standing ointment and without significant loss of available iodine or reduction in antibacterial activity over a reasonable shelf life time period is unknown.

SUMMARY OF THE INVENTION

The present invention most preferably includes the formation of an ointment including povidone-iodine which can be gamma irradiated without significant loss of the antimicrobial efficacy, without loss of viscosity or thickness and without a decrease in shelf life. The invention may have primarily primarily water as the main constituent being about two thirds of the mixture by weight. Purified water as used in the mixture is deionized or distilled water. A non-ionic gelling agent is by weight almost one-quarter of the mixture. The preferred agent may be a polyethylene and polyoxyproplene block copolymer surfactant About ten percent of the weight of the mixture is povidone-iodine in powder form, and the smallest portion of the mixture is a non-ionic low sudsing surfactant which is added at about one-fifth of a percent by weight. These ingredients are mixed in the purified water chilled to the range of about 2° C. to 9° C. At that temperature the ingredients are in the form of an easily mixed liquid. The mixture may be a liquid of viscosity about 1000CPS when cooled to approximately 3° C. thus greatly facilitating manufacturing and packaging. While the mixture may be mixed at a higher or lower temperature, the ease of mixing the liquid is preferred.

When the temperature of the liquid mixture is raised to room temperature, in particular above 9° C. and preferably around 20° C. to 25° C., a very high viscosity semi-solid mass referred to herein as a free standing ointment occurs. It is the elevation of the temperature which increases the viscosity of the mixture from that of a liquid to that of a semi-solid mass or free standing ointment. The ointment can be sterilized by gamma radiation in the range of 1.8 to 3.0 Mrad which results in a acceptable drop in available iodine concentration. The irradiated mixture has a long shelf life and is found to have extremely stable iodine concentration and physical properties when measured after storage at 60° C., 52° C., 42° C., 37° C., and room temperature for intervals of up to two years.

In the preferred method of forming the ointment the non-ionic low sudsing surfactant is added to and mixed with the purified water, chilled to between 2° C. and 9° C. Next, the povidone-iodine in powder form is added into the solution in a manner to prevent lumps from forming such that a solution can be made. The non-ionic gelling agent is added to that chilled solution to form a chilled liquid mixture. Warming the chilled liquid solution to room temperature produces, a free standing ointment in the form of a homogenous solution. The ointment has iodine but can be sterilized by gamma radiation without significant degradation of the antimicrobial efficacy of available iodine, without changing the semi-solid viscosity of a free standing ointment or without incurring instability during long term shelf life testing.

DETAILED DESCRIPTION

While this invention is satisfied by embodiments in many different forms, there is described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents, The iodophor ointment includes an antimicrobial povidone-iodine complex. In the preferred embodiment povidone-iodine powder in accordance with the standards of The United States Pharmacopeia The National Fomulary, referred to herein as USP, published by United States Pharmacopeial Convention, Inc., Rockville, Md. is used. As defined in the USP, the powder contains between 9% and 12% available iodine if calculated on its dried basis. The K-value of the povidone used in the povidone-iodine is typically K-30. The percent weight of the povidone-iodine powder is formulated to give the ointment an available iodine in the aqueous solution of about 0.85% to 1.2%. The antimicrobial properties of the ointment are provided entirely by the ability of the iodine portion of the povidone-iodine to kill microbes.

In order to make the ointment, chilled purified water in the range of 2° C. to 9° C. is used. The greatest portion of the mixture is chilled purified water which represents about two-thirds of the mixture by weight percentage. To obtain the right consistency of the ointment, a non-ionic gelling agent having the unique property of increased solubility with decrease in temperature of the water used provides the base of the free standing ointment. In the preferred embodiment, Pluronic F-127 is used as the non-ionic gelling agent and it is available from BASF Wyandotte Corporation, Parsippany, N.J. This material is in a powder form and is supplied as a gelling agent soluble in either hot or cold water. Pluronic F-127 is polyol being a block copolymer of, poly-(oxypropylene) poly-(oxyethylene) condensate and forms a gel in water at concentrations of about 20%. With this specific nonionic gelling agent the result is expected to be a wall-to-wall gelatinous material which will sustain a vibration when in the form of a gel.

The free standing ointment of the present invention retains the moist or wet appearance of a liquid on its surface but will not flow. The ointment formed is not gelatinous (in the sense that gels vibrate when suitably stressed). The preferred viscosity of the ointment was established by tests run with different concentrations of the non-ionic gelling agent added to the chilled purified water. Evaluations conducted on various samples having different concentrations of Pluronic F-127 in the purified water included solutions with concentrations of non-ionic gelling agent varying from 21% to 30%, by weight. All were prepared by mixing/dissolving the components at 3° C. with varying the amounts of pluronic F-127 and purified water in each mixture to make the different concentrations of non-ionic gelling agent. A test solution was prepared for use in formulating a series of samples each having a different viscosity. In the test solution the povidone-iodine powder is prepared from povidone K-30 powder and iodine powder mixed together. The non-ionic low sudsing surfactant was not added since it is in the mixture at less than a half of a percent by weight. These ingredients, in the basic solution are kept at their preferred weight percentages, so only the amount of the gelling agent was varied. Each mixture was then held at 3° C. until suspended air escaped and then each was mixed again to insure homogeneity. The Pluronic F-127 non-ionic gelling agent, used at various concentrations by weight concentration, is evaluated for the consistency at room temperature. Observations were made about the physical characteristics of each of the various Pluronic F-127 concentrations.

Sample 1 with a 30% weight concentration of nonionic gelling agent in chilled (3° C.) purified water had solid, undissolved Pluronic F-127. This concentration is excessive.

Sample 2 with a 27.5% weight concentration of non-ionic gelling agent in chilled (3° C.) purified water made a very thick nearly solid solution wherein still some Pluronic F-127 remained undissolved.

Sample 3 with a 25% weight concentration of the Pluronic F-127 non-ionic gelling agent in chilled (3° C.) purified water produced a solution which was complete but solidified at room temperature and showed a firm, dry character with no tendency to flow or separate.

Sample 4 with a 23.5% weight concentration of the Pluronic F-127 non-ionic gelling agent in chilled (3° C.) purified water resulted in the preferred embodiment as an ointment was prepared which appeared moist at room temperature. Although it is a solid and it does not flow at room temperature, the free standing gel has a wet looking surface appearance with no visible separation of the solid and liquid portions.

Sample 5 with a 22.8% weight concentration of the Pluronic F-127 non-ionic gelling agent in chilled (3° C.) purified water solution was not stable and separated after several weeks at room temperature.

Sample 6 with 22.5% weight concentration of the Pluronic F-127 non-ionic gelling agent in chilled purified water is very soft at room temperature. It tends to flow and it slightly separates after about 4 hours at room temperature.

Sample 7 with a 22% weight concentration of the non-ionic gelling agent in chilled purified water is very weak as it slowly flows. After a few minutes at room temperature separation becomes evident.

The practical range of concentration of Pluronic F-127 in water to make a free standing gel could range from 20% to 30% by weight depending on the temperature at which the mixture is to be stored and used, the exact consistency and shelf life required. Near 20% no semi-solid forms, the mixture exists as separate solid and liquid phases and at 30% no solution forms because there is insufficient water to dissolve the Pluronic F-127 non-ionic gelling agent. The specific percentage by weight of non-ionic gelling agent will vary to some degree depending on the particular non-ionic gelling agent or polyol used as a surfactant and the other ingredients specified for the mixture. For example, if the povidone K-value is higher than its typical K-30, the amount of non-ionic gelling agent necessary for an ointment could change.

In the preferred embodiment the povidone-iodine powder is prepared from povidone K-30 powder and iodine powder mixed together. The Pluronic F-127 non-ionic gelling agent is used at a 23.5% by weight concentration. The preferred mixture of Pluronic F-127 non-ionic gelling agent and purified water represents approximately 90% of the total mixture by weight. The antimicrobial povidone iodine powder USP (as specified in The United States Pharmacopoeia) is nearly the remaining 10%. The surfactant is less than one half of a percent.

The preferred range for the purified water is between about 62% and 69% percent by weight in the mixture. The preferred range for the non-ionic gelling agent, Pluronic F-127, is between about 20% and 30% by weight in the mixture. The preferred range for the povidone-iodine in the mixture is in the range of 10.4% to 11.5% by weight in the mixture. A non-ionic low sudsing surfactant is added to aid in the use of the free standing antimicrobial ointment in connection with skin oils. Oily skin on the patient to which this material is applied is effectively treated due to the addition of a slight amount of non-ionic low sudsing surfactant. Only a slight amount of such a material is generally required, in particular, less than a half of one percent by weight. The specifically preferred material is a polyol, Pluronic L-62LF, also from BASF Wyandotte Corporation.

While ranges have been given for the ingredients used in forming a free standing antimicrobial iodophor ointment, the preferred embodiment includes 65.4% chilled purified water, 23.5% Pluronic F-127, 10.9% povidone-iodine powder USP, and 0.2% Pluronic L-62LF. All of these percentages are by weight of the total mixture.

The viscosity of the free standing ointment is temperature dependent wherein viscosity increases with increasing temperature but does not present a problem to the manufacture of the finished product. The preferred mixture when manufactured at 3° C. and allowed to warm from 3° C. demonstrates increasing viscosity. At 3° C. the viscosity is 1000 CPS, at 4° C. 1125 CPS, at 5° C. 1425 CPS, at 6° C. 1688 CPS, at 7° C. 2150 CPS, at 8.5° C. 2650 CPS, and at 9° C. and above a free standing ointment occurs. The mixture can be maintained at low temperature as a liquid without adverse effects. The liquid form of the chilled mixture is ideal for easy filling during packaging. Accurate fill volumes and weights are obtained with the chilled liquid.

The ingredients of the preferred mixture are mixed in a temperature of 2° C. to 4° C. The main component, purified water, is held at 2° C. to 4° C. during the mixing operation. The addition of the ingredients is done in such a way that the temperature of the mixture throughout its manufacture is maintained in the 2° C. to 4° C. range. The free standing ointment does not occur until the temperature is raised to above 9° C. The preferred free standing ointment consistency (a solid with a moist liquid surface appearance) is stable at room temperature (about 20° C.).

The specific method used to form the free standing ointment of the preferred embodiment includes providing the chilled water in the 2° C. to 4° C. range, preferably about 3° C., adding the non-ionic surfactant Pluronic L-62LF and mixing, then adding the povidone-iodine powder USP in a manner adequate to avoid clumping so as to obtain a homogeneous solution without lumps. Finally, the Pluronic F-127, the block copolymer gelling agent is added. The entire mixture is maintained in the 2° C. to 4° C. range and is stirred for approximately one hour in order to produce a homogeneous liquid solution. The solution is allowed to warm up to above 9° C. and the liquid turns into a free standing ointment.

The appearance of the free standing ointment at room temperature is a solid with a moist or liquid surface. Because of the iodine, the iodophor ointment has a reddish brown color. It is an opaque substance with a mild, not sharp, iodine odor. The pH is in the range of 1.8 to 2.5 and the available iodine is between 0.90% and 1.2%. This is before the substance is gamma radiated for sterilization. After gamma radiation, the available iodine drops about 0.25% when the radiation level is 2.5 Mrad. The available iodine in the free standing ointment after radiation is relatively stable when tested by means of accelerated shelf life tests at elevated temperatures of 60° C., 52° C., 42° C., 37° C., and 25° C. Therefore, it is expected to have a commercial shelf life of greater than 10 years.

In order to prove that the product of the preferred mixture is useful, bactericidal efficacy testing was performed using the non-irradiated and irradiated product treated with 2.5 Mrads of gamma radiation. The test procedure used required nutrient agar in 100×15 mm petri dishes and pinicylinders with a cup size of approximately 8×8 mm. Microbial culture challengers were prepared in tryptic soybroth. The agar plates were inoculated by swabbing each plate with a selected test organism using sterile cotton swabs saturated with the culture resulting in confluent growth. Each cup was then filled with test agar. All agar plates were incubated for a minimum of 48 hours at 30° C. to 35° C. The recorded zone of inhibition is taken from measurements of the distance from the edge of the cup to the point where the microbial growth is inhibited. The greater the area of the inhibition zone the more effective the iodophor ointment will be in terms of killing microbes after the ointment is applied to the patients skin.

|  | Preferred Embodiment | |
| --- | --- | --- |
| Organism | Not Radiated | Gamma Radiated |
| *Staphylococcus aureus* | 16 mm | 13 mm |
| *Pseudomonas aeruginosa* | 7 mm | 7 mm |
| *Candida albicans* | 13 mm | 10 mm |
| *Escherichia coli* | 16 mm | 10 mm |

From the above results, it can be appreciated that the preferred mixture is effective over a measurable area as an antimicrobial for a range of organisms, even though it has been irradiated.

As mentioned the gamma radiation does effect the iodine slightly but not such that the active iodine is destroyed. To verify the improvement in viscosity and iodine stability after irradiation, a series of formulations were tested. The formulations are as identified in TABLE 1 which follows and are compared to a liquid iodine material in accordance with U.S. Pat. No. 4,427,631 which teaches a method for gamma sterilization of povidone-iodine solutions without degradation or gelation of povidone due to the presence of iodine and iodide ions. Iodide ions are required in that solution to prevent gelation of the povidone. Typically povidone-iodine powder, as described in the U.S.P. monogram, has iodine and iodide within the range covered in U.S. Pat. No. 4,427,631. In particular, U.S.P. powder contains 0.85 to 1.2% by weight of the amount of povidone.

Shown in TABLE 1 is an ointment formulation designated 167A which is the claimed and preferred mixture. A formulation with a cellulose thickened gel is also in TABLE 1. The advantages of the non-ionic gelling agent such as a polyoxyethylene and polyoxypropylene block copolymer surfactant will be apparent by comparison of the formulation 167A and the formulation thickened with cellulose which follow. Solution 41 is quite similar to the liquid antimicrobial of the U.S. Pat. No. 4,427,631 and is included as a material tested for purposes of verifying the iodine stability of the preferred mixture. The mixture in the third column in TABLE 1 is essentially the solution of U.S. Pat. No. 4,427,631 except for the absence of a small amount of Pluronics L62 LF, sodium phosphate and hydrogen peroxide and with the addition of a sodium iodate salt to prevent the loss of the iodine in the formulation. Formulation 167A shown in the second column performs well since the amount of available iodine remains essentially constant just as with the non-irradiated material. The formulation of column three diminishes in available iodine concentration by about one quarter.

TABLE I

| FORMULA IDENTIFICATION All values are % wt/wt | | | |
| --- | --- | --- | --- |
|  | Ointment 167A | Cellulose Thickened Gel | 10% Povidone-Iodine Solution 41% |
| Povidone-Iodine U.S.P. | 10.9 | 10.9 | 9.98 |
| Pluronic F127 | 23.5 | — | — |
| Hydroxylethyl Cellulose Cellucise QP-4400-H | — | 2.0 | — |
| Pluronic L62LF | 0.2 | 0.2 | 0.20 |
| $H_2O$ | 65.4 | 86.9 | 89.07 |
| Sodium Phosphate, Diabasic | — | — | 0.48 |
| Hydrogen Peroxide, 30 | — | — | 0.27 |
| Sodium Iodate | — | — | — |

In TABLE 1, note that, the radiation stable ointment formulation labeled 167A is essentially the same as the formulation in the column adjoining it entitled "Cellulose Thickened Gel". The significant difference is that Pluronic F127 (a polyoxyethylene, polyoxypropylene block copolymer surfactant) has been replaced by a hydroxyethylcellulose used to form the gel. The formulation in the third column is not a gel, it is a solution like that in the '631 patent. Each of these three formulations were irradiated by gamma radiation at 3.24 megarads. After irradiation, the percent available iodine and viscosity were measured. The data on viscosity appears on TABLE 2 and the data on stability is in TABLE 3.

TABLE 2

| | Radiation Stable Ointment 167A | | Cellulose Thickened Gel | |
| --- | --- | --- | --- | --- |
| Tests | Before Irradiation | Irradiated At 3.24 Mrads | Before Irradiation | Irradiated At 3.24 Mrads |
| Percent Available Iodine | 1.01 | 0.77 | 0.85 | 0.68 |
| Brookfield Viscosity, CPS | >2,000,000 | >2,000,000 | 910 | 86.6 |

The cellulose thickened gel formulation of TABLE 1, second column loses 90% of its viscosity after irradiation. Iodophors gels and ointments typically contain cellulosic materials as thickening agent and do not contain the claimed non-ionic gelling agent which is a polyoxyethylene and polyoxypropylene block copolymer surfactant. The comparison of formulations proves that Pluronic F127 resist in degradation viscosity due to gamma radiation and helps to prevent loss of iodine. Cellulose when used to thicken providon-iodine solutions does not resist radiation degradation of viscosity or prevent loss of available iodine.

Viscosity as described herein was tested by means of a Brookfield model LV (sapphire bearing) tester used to test drag induced by the particular formulation to be tested. The viscosity of the samples shown in TABLE 1 were measured by sensing the torque required to rotate a spindle immersed in a sample of the ointment. The spindle is rotated at a constant speed and the torque measured is proportional to the viscous drag on the immersed spindle. This in turn is proportional to the viscosity of the ointment. Each sample was tested for viscosity and the results obtained were recorded as the data shown.

Tests of againg characteristics on the radiation stable ointment 167A prepared and irradiated at 2.5 megarads and aged at 42° C. for a period of 130 days are in the Table 3 wherein a comparison of the irradiated mixture and a non-irradiated mixture are shown. The aging test was run over a period of time and the available iodine was measured during the term of the test.

TABLE 3

| | | Aging at 42° C.: Available Iodine (%) | |
|---|---|---|---|
| Days | Ointment 167A (Non-radiated) | Ointment 167A Irradiated at 2.5 Mrads | 10% Povidone-Iodine Irradiated at 2.0 Mrads |
| 0 | 0.98 | 0.88 | 1.01 |
| 12 | 0.95 | 0.77 | 0.97 |
| 46 | 0.96 | 0.84 | 0.85 |
| 70 | — | — | 0.81 |
| 82 | 0.94 | 0.77 | — |
| 100 | — | — | 0.74 |
| 130 | 0.95 | 0.91 | — |

To test the iodophor ointment for irritation with the maximum iodine content non-irradiated iodophor ointment of the formulation of the preferred embodiment was tested in four ways for safety and toxicity. The tests were primary skin irritation, dermal sensitization, primary eye irritation, and vaginal mucosal irritation. The primary skin irritation test proved negative, the dermal sensitization test proved negative, the primary eye irritation test proved positive, and the vaginal mucosal irritation test proved positive.

The primary skin irritation test was in accordance with the procedure in CFR Title 16, chapter II, part 1500.41. The testing done on the skin of rabbits includes applying the preferred iodophor ointment to gauze that is attached to shaved skin on the back of a rabbit. Two sites are selected, one slightly abraded and the other not. After 24 hours and 72 hours the two sites were examined. The dermal sensitization test is according to Buehler patch test procedure found in *Archives* of Dermatology, 91,171–175.

In another test guinea pigs are treated three times a week, Monday, Wednesday and Friday. The treatment consists of shaving the mid back area and applying ointment covered with tape (to prevent evaporation) for a period of six hours for each treatment. After the treatment the site is cleaned and examined for erythema or edema. At least 24 hours lapse between treatments. After 14 days, new animals plus the tested animals are again treated with the patch test to determine whether any of the tested animals have developed a sensitivity.

The primary eye irritation test was conducted with three rabbits wherein the ointment was put in the rabbits' lower conjunctival sac. The eyes were examined at 24, 48 and 72 hours after the ointment was placed. The scoring of the reaction is in accordance with *Illustrated Guide For Grading Eye Irritation By Hazardous Substances* from the U.S. Department of Health, Education and Welfare, Food and Drug Administration, Washington, D.C. The test procedure is in CFR 15, part 1500 of the Federal Hazardous Substances Act.

The last test was vaginal mucosal irritation. This test was run in accordance with CFR 21, part 58 according to Good Laboratory Practice Regulations. The procedure requires testing of three female rabbits on five consecutive days wherein two milliliters of the ointment were delivered to the vaginal vault by means of a catheter. Twenty-four hours after the last dose the rabbits were sacrificed and examined. Tissues were prepared for histological microscopic examination.

What is claimed is:

1. A method for making a sterilized antimicrobial ointment comprising the following steps:

chilling from about 62% to about 69% by weight of purified water to a temperature range of about 2° C. to about 9° C.;

mixing into the chilled purified water less than 0.5% by weight of a non-ionic low sudsing surfactant wherein said surfactant is a poly(oxypropylene)poly(oxyethylene) condensate having an average molecular weight of 2450;

mixing into the chilled purified water from about 9% to about 12% by weight of povidine iodine wherein said povidine iodine has an intrinsic viscosity of K-30 and is a powder mixture of povidine and iodine to form a homogenous solution;

mixing from about 20% to about 30% by weight of a non-ionic gelling agent wherein said non-ionic gelling agent is a pluronic polyol comprising an ethylene oxide to propylene oxide ratio of about 2.9 to about 1 into the chilled homogenous solution to form a liquid solution at a temperature from about 2° to about 9° C.;

increasing the temperature of the homogenous solution to above 9° C. to form an ointment mixture; and irradiating the free standing ointment mixture at about 1.3 Mrads.

* * * * *